(12) United States Patent
Jo et al.

(10) Patent No.: US 10,390,907 B2
(45) Date of Patent: Aug. 27, 2019

(54) METHOD FOR PRODUCING TRAYS FOR BRACKETS

(76) Inventors: Yong-Min Jo, Dusseldorf (DE); Andreas Urban, Hagen (DE)

(*) Notice: Subject to any disclaimer, the term of this patent is extended or adjusted under 35 U.S.C. 154(b) by 722 days.

(21) Appl. No.: 14/009,739

(22) PCT Filed: Apr. 5, 2012

(86) PCT No.: PCT/EP2012/056349
§ 371 (c)(1),
(2), (4) Date: Dec. 15, 2013

(87) PCT Pub. No.: WO2012/136803
PCT Pub. Date: Oct. 11, 2012

(65) Prior Publication Data
US 2014/0178828 A1    Jun. 26, 2014

(30) Foreign Application Priority Data
Apr. 5, 2011  (WO) .................. PCT/EP2011/055258

(51) Int. Cl.
*A61C 7/14*    (2006.01)
*A61C 7/00*    (2006.01)

(52) U.S. Cl.
CPC .............. *A61C 7/146* (2013.01); *A61C 7/002* (2013.01)

(58) Field of Classification Search
CPC .............. A61C 7/00; A61C 7/14; A61C 7/146
See application file for complete search history.

(56) References Cited

U.S. PATENT DOCUMENTS 3,738,005 A    6/1973  Cohen et al.
4,360,341 A  * 11/1982  Dellinger ............... A61C 7/146
                                                       433/24

(Continued)

FOREIGN PATENT DOCUMENTS

EP    1570803 A2    9/2005
EP    1941842 A2    7/2008
(Continued)

OTHER PUBLICATIONS

International Search Report dated Jul. 31, 2012, with regard to corresponding International application PCT/EP2012/056349.

(Continued)

*Primary Examiner* — Cris L. Rodriguez
*Assistant Examiner* — Hao D Mai
(74) *Attorney, Agent, or Firm* — Abel Schillinger, LLP

(57) ABSTRACT

A method can include producing a real model, including a reproduction of at least sections of at least two tooth crowns of teeth in a jaw and contains bracket reproductions or brackets associated with the reproductions of the tooth crowns; and producing at least two trays by producing at least one impression of the real model, wherein the trays each comprise an impression of at least one tooth crown part of the at least two tooth crowns and at least one bracket part of the at least two bracket reproductions or brackets, wherein the at least one bracket part, viewed from the occlusal surface of the associated tooth crown, extends vertically to at most the end of the wire guide and/or the end of the first undercut of the bracket and/or bracket reproduction, which is arranged after the upper wing in the view from the occlusal surface.

11 Claims, 2 Drawing Sheets

(56) References Cited

U.S. PATENT DOCUMENTS

| | | | | |
|---|---|---|---|---|
| 4,626,208 | A | * | 12/1986 | Hall ................... G01S 13/755 433/3 |
| 4,657,508 | A | * | 4/1987 | Dellinger ............... A61C 7/146 433/24 |
| 5,114,339 | A | * | 5/1992 | Guis ................... A61C 7/146 433/24 |
| 5,863,198 | A | * | 1/1999 | Doyle .................. A61C 7/146 433/3 |
| 5,938,435 | A | * | 8/1999 | Raspino, Jr. ............ A61C 7/12 433/2 |
| 5,971,754 | A | * | 10/1999 | Sondhi ................. A61C 7/146 433/24 |
| 6,123,544 | A | * | 9/2000 | Cleary ................. A61C 7/146 433/24 |
| 7,473,096 | B2 | * | 1/2009 | Cinader, Jr. ............ A61C 7/146 433/24 |
| 7,762,815 | B2 | * | 7/2010 | Cinader, Jr. ............ A61C 7/146 433/213 |
| 2005/0074716 | A1 | * | 4/2005 | Cleary ................. A61C 7/146 433/3 |
| 2006/0084026 | A1 | * | 4/2006 | Cinader ................ A61C 7/146 433/24 |
| 2006/0084030 | A1 | * | 4/2006 | Phan ................... A61C 7/146 433/72 |
| 2007/0031775 | A1 | | 2/2007 | Andreiko |
| 2007/0087302 | A1 | | 4/2007 | Reising et al. |
| 2008/0227050 | A1 | | 9/2008 | Marshall |
| 2009/0220920 | A1 | * | 9/2009 | Primus ................. A61C 7/16 433/226 |
| 2010/0159413 | A1 | | 6/2010 | Kuo |
| 2010/0279243 | A1 | * | 11/2010 | Cinader, Jr. ............ A61C 7/16 433/3 |
| 2013/0196279 | A1 | * | 8/2013 | Curiel ................. A61C 7/002 433/3 |

FOREIGN PATENT DOCUMENTS

| | | |
|---|---|---|
| FR | 2959929 A1 | 11/2011 |
| WO | 2007129833 A1 | 11/2007 |
| WO | 2009020282 A1 | 2/2009 |

OTHER PUBLICATIONS

International Search Report dated Jun. 12, 2011, with regard to corresponding International application PCT/EP2011/055258.

* cited by examiner

METHOD FOR PRODUCING TRAYS FOR BRACKETS

CROSS-REFERENCE TO RELATED APPLICATIONS

The present application is a National Stage of International Application PCT/EP2012/056349, filed Apr. 5, 2013, which claims the benefit under 35 U.S.C. 119(e) of PCT/EP2011/055258, filed Apr. 5, 2011; the disclosures of these applications are expressly incorporated by reference herein in their entireties.

BACKGROUND OF THE DISCLOSURE

1 Field of the Disclosure

The invention relates to a method for producing individual trays for positioning brackets.

Brackets are used in various forms with further aids, such as in particular wires, for the orthodontic correction of malocclusions. For this purpose, generally at least two brackets or bands are applied to or over crowns of teeth. This generally involves brackets being adhesively attached to tooth crowns. Brackets may in this case be adhesively attached both to the buccal surface and to the lingual surface of the teeth. The brackets generally have a slot for receiving an arch bar, in particular an archwire, in particular with a rectangular cross-sectional area. In this case it is possible to transfer forces and torques to the teeth via the arch bar, in order in this way to influence their position and alignment.

Originally, laboriously bent bands that had to be adapted for the various stages of treatment were used. By contrast, the straight-wire technique has become established, a technique in which the brackets are shaped in such a way that there is generally no need for laborious bending of the band. In particular, movements of a first, second and third order are rendered superfluous by corresponding formation of the brackets. Thus, for example, the bendings of the first order are replaced by variation of the bracket base height. As a result of the specifications that are variously incorporated in the brackets, such brackets are also referred to as programmed bracket appliances. When brackets of the straight-wire technique are used, the exact positioning of the brackets on the teeth plays a particularly important role, since only then can the incorporated specifications be transferred to the teeth in the desired way.

PRIOR ART

Numerous techniques are known to facilitate the work here of the orthodontist when applying the bracket and ensure reliable treatment and avoid errors. For example, it is known from EP 1 941 842 A2 to use or produce bracket feet areas that are adapted to the individual surface of the teeth, so that each bracket can only be attached to the respective tooth in the previously planned alignment and placement.

In addition, it is known from U.S. Pat. No. 3,738,005 to fix the brackets on a setup and cast a tray thereover. Subsequently, the tray with the brackets received therein is broken away from the setup and, with the aid of the tray, the brackets placed therein are transferred to the patient.

It is also known to produce the trays from a virtual set-up by rapid prototyping.

BRIEF DESCRIPTION OF THE DISCLOSURE

However, the known aids and methods all have disadvantages. For instance, they are either not very accurate and/or involve a great amount of effort and high costs. In particular, the individual, exactly fitting fabrication of bracket feet areas is laborious and also leads to significantly less stable brackets. In addition, the covering of a large part of the surface of the tooth must be counted as a negative aspect. Attaching the brackets is hindered thereby. On the other hand, the initially manual fixing on a setup, as in U.S. Pat. No. 3,738,005, already entails inaccuracies. In addition, the casting over of the brackets and their subsequent removal from the setup, carried out by applying comparatively great force, is accompanied by disadvantages with respect to accuracy. Trays manufactured by rapid prototyping often have problems with durability. In addition, removal of the trays after attachment of the brackets to the tooth crown is often problematic.

It is consequently an object of the invention to provide a method by which a tray for the placement of brackets can be created in an easy way and which allows brackets to be placed quickly and with great accuracy.

To this end, keeping free a large area of operation is advantageous. Also an easy separation of the trays from the attached brackets should be assured by otherwise sufficient hold of the brackets in the tray.

This object is achieved by a method and a tray described in the present disclosure.

The method according to the invention comprises the following steps:

At least one actual, in particular one-part, model is produced, the at least one model being a replica of at least portions of at least two tooth crowns of teeth located in a jaw and comprising bracket replicas or brackets assigned to the replicas of the tooth crowns. Connections of a planned size and shape between a bracket and a tooth crown, in particular virtual connections, may also be comprised. Consequently, at least one model is created, and is in particular a one-part model. In this case, at least a portion of each of the two tooth crowns with assigned bracket replicas or brackets is replicated by the model. In addition, the bracket replicas or brackets are replicated in reality and, if present, the respective connections are also reproduced in the actual model. Consequently, a model of at least a respective portion of two tooth crowns with the assigned brackets and any connections that may be arranged therebetween is produced. In particular, an actual model of at least one or two entire jaws or the tooth crowns located in at least one jaw or in at least two jaws is created. This advantageously involves also actually reproducing in the model all the assigned brackets and any connections arranged therebetween.

In this case, it is sufficient to reproduce a sufficiently large part of each tooth crown and each bracket, and of any connection there may be, to be able later to produce from the model a tray that is definitively oriented on the tooth crown and clearly defines the position of the bracket. If trays are formed over multiple tooth crowns, definitive orientation in relation to these multiple tooth crowns is sufficient.

The modelled bracket replicas must also only be reproduced in a sufficient part or with sufficiently faithful detail to allow the actual brackets to be later arranged reliably and stably in the predetermined orientation in the tray.

In the creation of the model, the arrangement of the individual tooth crowns in relation to one another must only be reproduced with respect to the tooth crowns in the model on the basis of which a common tray is to be created in the end. Otherwise, the models of the individual tooth crowns with the assigned bracket replicas and, if present, the respective connections may be placed freely in space. This is advantageous for easy creation of the model, and in particular for the subsequent creation of the tray. Thus, in particular whenever each tray is to be created only on the basis of one tooth crown model, each tooth crown model can be arranged at a distance from the others, in particular multiple models or all models spaced apart next to one another.

The trays are distinguished by the fact that they respectively comprise an impression of only in each case at least one tooth crown part of the at least two tooth crowns and only in each case at least one bracket part of the at least two bracket replicas or brackets. In this case, the at least one bracket part respectively extends vertically, as seen from the occlusal surface of the assigned tooth crown, at most up to the end of the wire guide and/or up to the end of the first undercut of the bracket and/or bracket replica that is arranged after the upper wing when viewed from the occlusal surface.

This provides sufficient retention, a large-sized free working space and at the same time great precision and a very simple and rapid manner of production.

Brackets usually have wings, in particular two wings, which extend above and below the wire lead-through. The wings are partially curved slightly towards the bracket foot or, when viewed from the plane of the occlusal surface, create undercuts or comprise undercuts. These are reproduced in the bracket part.

When viewed from the plane of the occlusal surface, the wire guide of the bracket also usually comprises undercuts. These may likewise be included in the model. However, not included in the model, according to the invention, when viewed from the plane of the occlusal surface, is the extent of the bracket beyond the wire lead-through. Depending on the embodiment, in particular if thermoforming film is used when taking the impression, undercuts of the wire lead-through do not comprise part of the bracket part either. Then, when viewed from the plane of the occlusal surface, the bracket part extends in particular up to before the beginning of the wire lead-through or the undercuts thereof.

In general, however, it should be ensured that the bracket part is chosen to be sufficiently large that a connection between the tooth crown replica and the bracket replica is included in the model. As a result and due to any undercuts that may be present, a sufficient and exact retention of the bracket in the tray is ensured.

It is also advisable depending on the application to choose the extent of the bracket part up to within the wire lead-through, in particular to the middle thereof. This is sometimes necessary in order to include a connection between the tooth crown replica and the bracket replica, but may otherwise also contribute to better retention of the bracket in the tray.

However, a bracket part going beyond the wire lead-through should not be chosen, since it is then more difficult to detach the adhesively bonded brackets and the working area is unduly restricted.

The tooth crown part is advantageously chosen such that, seen from the plane of the occlusal surface, it extends up to the end of the bracket part.

The model of each tooth crown advantageously comprises no more than the corresponding tooth crown part and, of each bracket or bracket replica, no more than the corresponding bracket part. This allows direct production of the trays to be achieved.

In an alternative embodiment it is possible that the model of one or more tooth crowns comprises more than the corresponding tooth crown part and/or the model of one or more brackets or bracket replicas comprises more than the corresponding bracket part. In this case, after the taking of the impression, the corresponding trays then likewise comprise more of an impression of the tooth crown or of the bracket than an impression of the tooth crown part or of the bracket part. After the taking of the impression, according to the invention, these trays are then shortened such that, of the tooth crown, they only have an impression of the tooth crown part and/or, of the bracket, they only have an impression of the bracket part. This may take place for example by grinding or milling.

When viewed from the occlusal surface, the tooth crown part advantageously extends at most only up to before the first undercut of the tooth crown.

Creating an actual model can be precede creating a virtual setup of at least two tooth crowns of teeth located in a jaw can be. The setup is understood as meaning the desired arrangement, or arrangement to be achieved, of the teeth that are actually located in the jaw. This replicates at least two teeth, in particular at least a complete jaw. The setup generally only comprises the crowns of the teeth and not the roots, since the corresponding impression, of an actual or virtual nature, generally only replicates the tooth crowns. These are then transferred into the setup and arranged there as desired.

For this purpose, actual impressions of tooth crowns are generally taken according to prior art techniques, subsequently cast back into positives and then sawn, and subsequently positioned as desired, generally in wax. Such a setup usually forms the basis for the creation of aids for influencing tooth positioning. The setup is generally fitted into an articulator, in order to be able to reproduce the movement of the jaws.

However, such a setup may preferably also take place virtually after the recording of the initial situation with the patient.

This is followed by the arrangement of a respective bracket replica in relation to at least two replicas of the tooth crowns in the setup. The bracket replicas are advantageously virtual replicas of actual brackets, in particular at least a large part of the outer contours thereof. In this case, each virtual bracket replica has a bracket replica foot area. The bracket replica foot area is advantageously a replica of an actual bracket foot area. With such a bracket foot area, a bracket is arranged on a tooth and adhesively bonded to it. The adhesive thereby comes to lie between the bracket foot area and the tooth.

The arrangement is advantageously performed in a straight-wire arrangement. This is understood as meaning an arrangement of the bracket replicas or the brackets that allows use of the straight-wire technique. In particular, in the case of a straight-wire arrangement, the placement of the brackets is of decisive importance, so that in the case of such an arrangement the advantages of the invention particularly come into effect.

In the arrangement of the bracket replicas, an intermediate space may remain between the bracket replica foot areas and the replicas of the tooth crown surface. The intermediate space that is possibly present between the bracket replica foot areas or the bracket foot areas and the tooth crown replica is later bridged by adhesive.

Creating a connection between the bracket replica foot areas and the respective replication of the tooth crown can follow for bridging intermediate spaces between bracket replica foot areas and the respectively assigned replica of the tooth crown in cases in which the bracket replica foot area does not lie against the replica of the tooth crown, in particular not with surface area contact. Such a creation of the connection is advantageously performed fully automatically. Advantageously, the shortest connection between bracket replica foot areas and the respective replica of the tooth crown is bridged. Advantageously, the bridging has in this case a sufficient thickness, so that a model that is correspondingly later fabricated is statically stable. Advantageously, the bridging is formed all the greater in cross section the longer it is. The bridging in this case respectively runs between a bracket replica foot and the replica of the tooth crown to which the respective bracket replica foot area is assigned. If the bracket replica foot area already lies against the replica of the tooth crown, in particular in surface area contact, creation of a bridge is not required, since the bridging is already ensured by the bracket replica foot area.

The connection is advantageously formed in cross section over the entire lateral extent of the bracket replica foot area, so that partial impressions later created on the model do not engage in undercuts between the tooth crown and the bracket foot area. It is also conceivable for the connection on the tooth crown or the replica thereof to be advantageously formed in cross section greater than or identical to the bracket foot area. This makes particularly clean handling of the later adhesive bonding possible.

To produce the actual model, instead of a transformation back into the initial situation with the patient, the replicas of the tooth crowns are advantageously aligned with one another in such a way that the wire guides of the bracket replicas or brackets are in line. As a result, a model with wire lead-throughs in line is created, which greatly facilitates the production of the trays and also already of the mould for producing the tray that comprises the actual model. This is the case in particular if the length of the bracket part is based on the wire lead-through and in this respect is chosen to be the same in all bracket parts, that is to say for example the bracket parts all extend up to the upper beginning of the wire lead-through or all extend up to the middle of the wire lead-through or all extend up to the lower end of the wire lead-through, in each case seen from the occlusal surface of the tooth crown as above.

It may also be advantageous to fabricate the model, including further walls, bases and/or delimitations, in particular to fabricate a complete casting mould as a model, or to bring the model into a mould, in particular a reusable mould, in such a way that a finished casting mould for a tray to be cast is produced.

In particular in the case of the arrangement of multiple tooth crown/bracket units in a model, the provision of such walls between the individual tooth crown/bracket units of the model is preferred when taking an impression by casting, since individual trays can then be created in a simple way on the basis of a single model.

The creation of the actual model may be performed for example by rapid prototyping and/or three-dimensional printing. In this case, additional walls, bases, mounts and the like can be created in one operation.

This is followed by the production of trays, in particular at least two trays, in particular flexible trays, by producing partial moldings of the at least one actual model that are respectively suitable for receiving at least partially one of the at least two tooth crowns and at least partially a bracket replica that is moreover assigned to the respective tooth crown, or a corresponding actual bracket, receiving them in such a way that the arrangement of the bracket replica and of the replication of the tooth crown is reproduced in reality by the bracket received and the tooth crown received. Therefore, in particular at least two trays are created, each for receiving at least one bracket, in particular one each, which trays are respectively designed such that they receive a part of the bracket, and a part of the tooth crown in such a way that the planned arrangement between the tooth crown replica and the bracket replica is later reproduced in reality by the tooth crown and the bracket.

The production of such trays may be performed for example by overmoulding or by thermoforming of thermoforming film.

When taking an impression by casting, a compound that shrinks during curing is advantageously used. Such shrinkage allows the clamping effect of the tray to be increased. Such shrinkage may also be taken into consideration in the creation of the model and the model may be partly produced slightly enlarged, in order for example to increase the clamping effect only in some regions, in particular only on the bracket. Thus, for example, the tooth crown part may be included in the model in a correspondingly enlarged form.

Advantageously, a tray that only comprises one tooth crown is created per bracket. This makes it possible for the brackets together with the trays to be introduced particularly easily into the oral cavity of the patient. This can also be made by disjoining n impression. However, trays for multiple tooth crowns or multiple brackets may also be created. In an embodiment that is not preferred, in the end only one tray that can receive all of the assigned brackets is provided.

Advantageously one actual model per replica of tooth crowns provided with a bracket replica is created in the production of the actual model. The separate creation of a model per tooth crown replica with an assigned bracket part allows particularly easy production of a corresponding tray.

In another embodiment, advantageously a single actual model of all the replicas of tooth crowns, provided with a bracket replica, and the bracket replicas and connections of one or two jaw of a human is first created, and this is subsequently divided up such that each fragment is a replica of at least parts of only one tooth crown with a bracket and possibly a connection. Common production may lead to savings in the creation of the model; in particular, it is then initially only necessary to keep one model. In particular, in the case of rapid prototyping, a single production compound can be used. Subsequent sawing apart in turn makes it possible for corresponding trays to be easily produced. However, in a single model the individual tooth crown part/bracket part units can also be separated from one another such that individual trays can be produced on the one model. However, when taking an impression by casting, separating walls may thus also be created at the same time when producing the actual model, so that individual trays can be created unproblematically without sawing them apart.

Thus, for example, all the models of tooth crowns may be arranged in a series or in a number of series running parallel to one another, in particular straight lines. One or two series per jaw would be suitable here in particular. In this case, the series are advantageously connected to one another and produced together from one piece. Alternatively or in addition, a certain intermediate space may be left between the individual models of the tooth crowns, so that for example the individual models of the tooth crown replicas with the brackets and possible connections can be found at a certain distance apart on a straight bar. A distance is also advantageously provided between parallel series, so that the tooth crown part/bracket part units do not touch. The connections between the units can then be created for example by a common mount. Such a model can be produced particularly easily and in a standardized form and can in particular be handled well in the further procedure. In particular, with a corresponding distance between the individual tooth crown part/bracket part units, there is no need for sawing up for the production of individual trays.

It is advantageous to proceed in the creation of the virtual setup by initially creating an actual impression of at least two tooth crowns of teeth located in a jaw and then creating a virtual replica of the impression, and subsequently producing a virtual setup on the basis of the virtual impression. In this case, the actual impression will initially be a negative impression. It is subsequently possible first to produce a positive of the impression and then to transform this into a virtual replica. Alternatively, a virtual replica may also be produced immediately and directly from the actual negative impression and then converted into a virtual positive, on which the creation of the virtual setup is then based. It is also conceivable to continue working with a virtual negative impression and to create a negative virtual setup and arrange the bracket replicas or bracket replica foot areas on the boundary areas thereof.

In another alternative it is advantageous to proceed in the creation of the virtual setup by initially creating an actual impression of at least two tooth crowns of teeth located in a jaw and subsequently producing an actual setup on the basis of the actual impression. This may be performed for example by sawing up and setting in wax. Subsequently, a virtual replica of the actual setup is created and a virtual setup is thus produced. In the creation of the actual impression, generally a negative impression is initially obtained, and then an actual positive impression is created from it before an actual setup is produced.

The transformation into the virtual form may be respectively performed by various methods, such as for example scanning by laser or reconstruction from computed tomography data.

In another procedure, the creation of the virtual setup is advantageously carried out by initially producing a virtual replica of at least two tooth crowns of teeth located in a jaw, in particular by optical measurement of the at least two tooth crowns. On this basis, a virtual setup is then produced. The creation of the virtual impression may be performed for example by laser scanner directly in the oral cavity of the patient. Alternatively, it may also be produced on the basis of an X-ray CT. Other methods are conceivable in principle.

The selection of a bracket replica from a bracket library is advantageously carried out first, the bracket library consisting of a set of virtual replicas of brackets that are actually available. Such a selection allows the production step concerning brackets to be simplified, by relying on standard components. The selection from various brackets makes it possible however for treatment to be specially adapted.

It is advantageous to proceed in the creation of the tray by initially dividing up the actual model into portions having only one tooth crown replica with a bracket replica and possibly a connection and subsequently producing partial impressions. Alternatively, depending on the application, it may be advantageous to proceed by initially making a partial molding on the basis of at least models of the at least two tooth crowns and subsequently dividing up the partial molding, in particular such that each part produced only represents a partial impression of a tooth crown with an assigned bracket and possibly a connection.

The bracket replicas are advantageously virtual replicas of actual one-part brackets. One-part brackets are those which, apart from movable parts, in particular for locking devices, are formed as one part. One-part brackets can be produced particularly easily and have particularly good stability. The use of particularly adaptable, individually fabricated and/or individually adapted brackets, in particular those of which the length is adaptable or is adapted, is not necessary in the case of the present method, since an alignment and setting of the distance on the basis of the trays is possible without any problem.

Advantageously, bracket replica foot areas of a thickness that is increased in comparison with the actual bracket foot areas of the respectively replicated actual bracket by a minimum adhesive material thickness of the adhesive material that can be used for adhesively bonding the bracket to the tooth crowns are advantageously used. If the brackets were arranged in the virtual replication or the virtual bracket replicas were arranged in the virtual arrangement immediately on the virtual tooth crown replicas, in the end there would in fact be no space for adhesive compound in the placement of the brackets with the aid of the tray, so that the interposed adhesive material compound would give rise to inaccuracies, in particular on account of the deformation of the elastic tray, and/or the adhesive would be excessively forced out of the adhesive area, so that reliable adhesive bonding would not be possible. For this reason, allowance for a minimum thickness of the adhesive material is already advantageously made in the bracket replica foot areas, so that unproblematic adhesive bonding is later possible. Greater distances can be bridged without any problem by more adhesive compound. In this case, the alignment is provided by the tray.

Actual brackets corresponding to the bracket replicas or the brackets are advantageously set into the partial impressions such that they are arranged there in the same way as the bracket replicas or brackets were arranged in the production of the at least one actual model. As a result, the brackets are arranged in the partial moldings, that is to say in the trays, in such a way that they can be transferred with an exact fit into the patient, or onto the tooth crowns of the patient, to be specific precisely as planned in advance.

For this purpose, the brackets are advantageously screwed into the partial impressions and thereby screwed into an undercut or undercuts of the partial impressions. Insertion into undercuts without screwing is either not possible or often changes the partial impressions in such a way that the brackets are then only retained poorly or not at all any longer. Insertion by screwing allows the bracket to be inserted or screwed into undercuts, for example on the upper wing and/or the wire lead-through, without the retaining effect in the tray being noticeably reduced.

The partial moldings are advantageously produced by thermoforming of thermoforming film, in particular elastic tough thermoforming film. In this way, corresponding partial moldings, that is to say trays, can be produced particularly reliably, quickly and inexpensively.

A gripping aid may be provided on each tray, to facilitate the gripping and positioning of the tray in the oral cavity of the patient. For this purpose, a columnar structure may be provided in particular on the tray, in particular on the upper side thereof, which is the side that is facing the occlusal surface. This structure may have in particular a narrowing, which can be at least partially enclosed by a corresponding instrument, for example tweezers. The gripping aid is in this case rotationally symmetrical about at least one axis and, in interaction with the instrument, offers mobility at least about this axis. The gripping aid may, for example, be formed from metal and have in particular a base by which it is connected to the tray. This may take place by adhesive attachment, by fusing in or by casting in when creating the tray by casting. The narrowing is arranged in particular between the tray and a region with a greater diameter. The narrowing may also be arranged between an end hemisphere to sphere with a greater diameter and the tray. The instrument can then at least partially enclose the sphere and also engage in the narrowing such as to rule out the possibility of slipping off from the gripping element. In this way it can also be ensured that there is mobility between the gripping aid and the instrument that goes beyond the mobility about the axis of symmetry. In particular, tilting between the axis of symmetry and the longitudinal axis of the instrument through a defined angular range is then also possible. In particular, the instrument has two shells with quarter- to hemispherical clearances, which are made to match the end hemisphere to sphere in diameter and by which the end hemisphere to sphere can be engaged. In particular, the instrument, which may be included in a system comprising an instrument and at least one gripping aid or at least one tray with a gripping aid, is formed such that it does not release a gripping aid once gripped without force being externally applied, and release can be achieved by correspondingly applying force to the instrument.

The object is also achieved by a tray described in the present disclosure, the comments made with respect to the method applying with respect to the extent of the tray and being applicable to the tray.

BRIEF DESCRIPTION OF THE DRAWINGS

In the figures, which are schematic and given purely by way of example.

DETAILED DESCRIPTION OF THE DISCLOSURE

Figure 1:
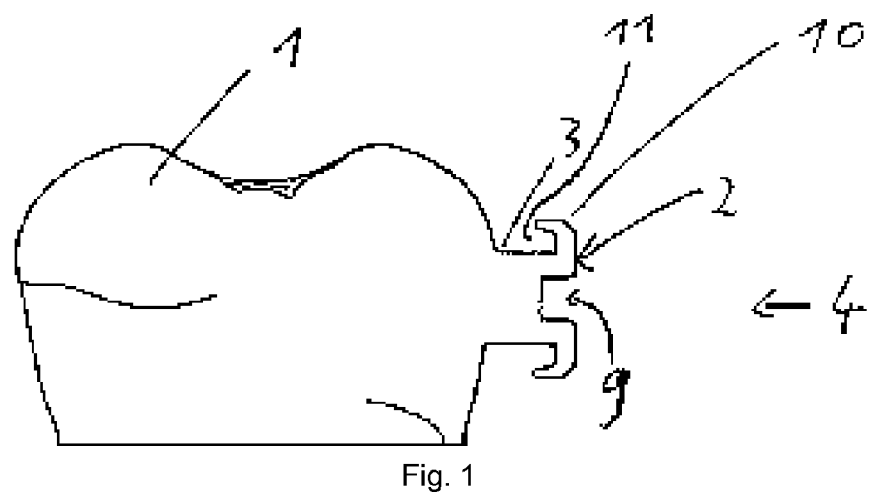
FIG. 1 shows a view of an entire replica

In FIG. 1 an entire replica is shown, comprising a tooth crown replica 1, a connection replica 3 and a bracket replica 2. The bracket replica 2 has a wire lead-through 9 as well as two wings 10 and wing undercuts 11.

According to the invention, however, such an entire replica 4 is not used. Rather, a model 5 such as that shown in FIG. 2 is used instead of such a replica.

Figure 2:
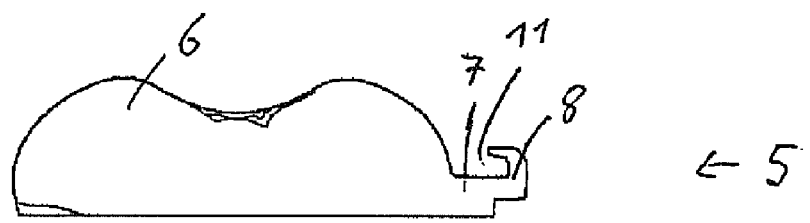
FIG. 2 shows a view of a model

FIG. 2 shows a model 5 comprising a tooth crown part 6, a connection part 7 and a bracket part 8. It can be seen that the bracket part 8 has a wing undercut 11. A part of the wire lead-through 9 or the undercut thereof is also included in the bracket part 8. As a result, the bracket part 8 has two undercuts. In this embodiment, the tooth crown part 6 also has a small undercut, which can be seen on the left side.

On the basis of such an actual model, a tray can be produced in various ways.

Figure 3:
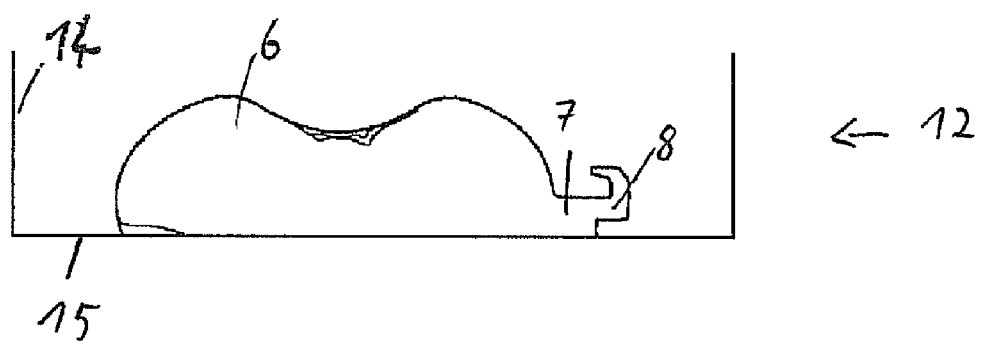
FIG. 3 shows a view of a mould

FIG. 3 shows a mould 12 for the production of a tray by casting. Apart from the model 5, which has already been shown in FIG. 2 and which comprises a tooth crown part 6 as well as a connection part 7 and a bracket part 8, the mould 12 comprises a base 15 and walls 14. The walls 14 have the effect of creating a closed mould 12, which can be filled with corresponding material. This allows the tray to be produced.

Figure 4:
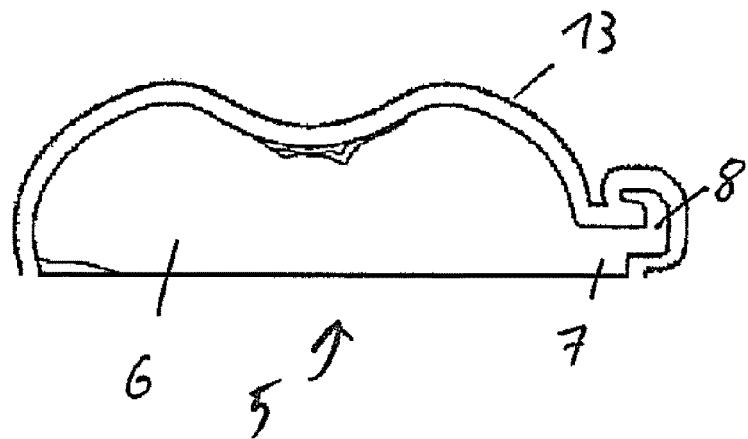
FIG. 4 shows a view of a model with a tray

FIG. 4 shows the production of a tray 13 by using a thermoforming film. A model 5 comprising a tooth crown part 6, a connection part 7 and a bracket part 8 can be seen. A tray 13 is produced on this model by thermoforming of a thermoforming film.

Figure 5:
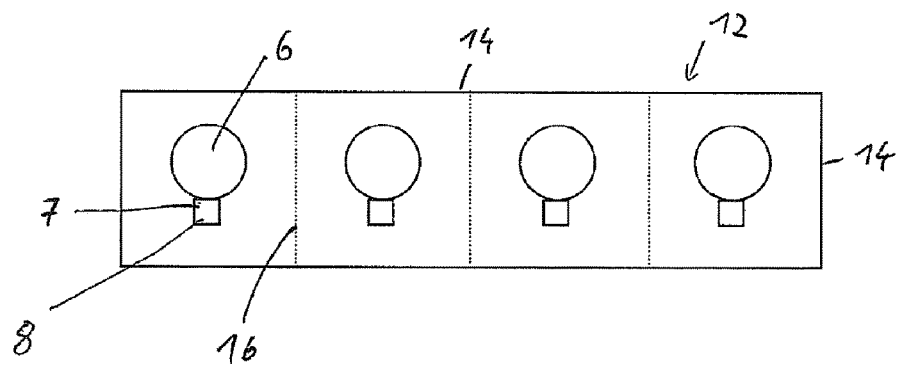
FIG. 5 shows a view of a single-series mould

FIG. 5 shows a mould 12, comprising multiple tooth crown parts 6, connection parts 7 and bracket parts 8. The mould 12 is enclosed by walls 14. Likewise shown are dashed cutting lines, where the tray produced by casting can be divided up, so that then individual trays are produced.

Figure 6:
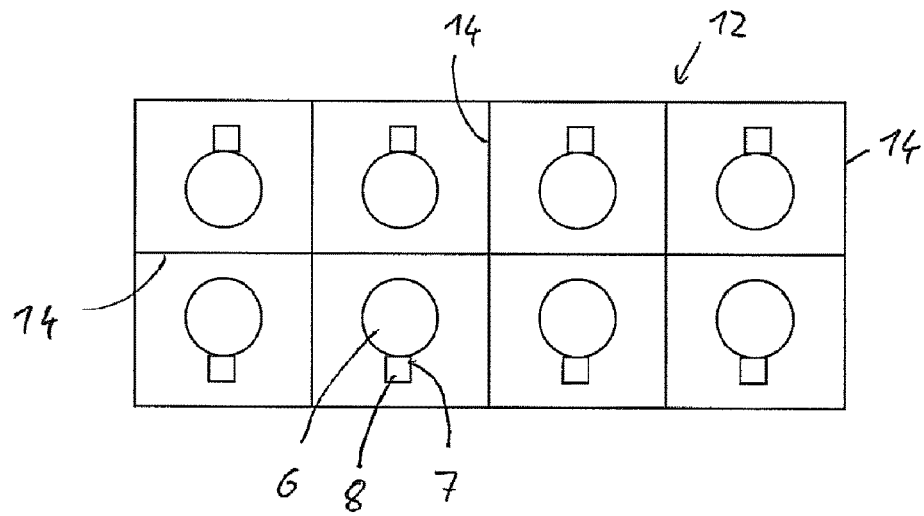
FIG. 6 shows a view of a two-series mould

FIG. 6 shows a two-series mould 12, comprising eight tooth crown parts 6, connection parts 7 and bracket parts 8. The mould 12 not only has exterior walls 14. Rather, it also has interior walls 14, which run horizontally and vertically and divide the mould 12 up into eight individual moulds, with the aid of which eight individual trays can be produced directly in a simple operation.

LIST OF DESIGNATIONS

1. Tooth crown replica
2. Bracket replica
3. Connection replica
4. Entire replica
5. Model
6. Tooth crown part
7. Connection part
8. Bracket part
9. Wire lead-through
10. Upper wing
11. Wing undercut
12. Mould
13. Tray
14. Wall
15. Base
16. Cutting line

What is claimed is:
1. A method of producing individual trays for positioning orthodontic brackets on a patient's teeth, the method comprising:
   a) producing a model, the model comprising a replica of at least portions of at least two tooth crowns of the patient's teeth;
   b) arranging a bracket replica or bracket replica part on each of the at least portions of the at least two tooth crowns of the model, wherein the bracket replica or bracket replica part comprises a coronal wing; and wherein arranging of the bracket replica or bracket replica part includes positioning the bracket replica or bracket replica part in a desired position on an exterior surface of each of the at least portions of the at least two tooth crowns such that the bracket replica or bracket replica part is extending on said exterior surface in an occlusal-gingival direction; and
   c) producing at least two trays, each of said at least two trays being produced by forming at least one impression of the model with the positioned bracket replica or bracket replica part on each of the at least two tooth crowns thereon; the at least two trays each comprising: an impression of at least an occlusal portion of each of the at least two tooth crowns and of at least a coronal portion including at least the coronal wing of the bracket replica or bracket replica part, wherein said impression extends gingivally at most to an end of a wire guide of the bracket replica or bracket replica part, the wire guide being arranged gingivally of the coronal wing of the bracket replica or bracket replica part when viewed vertically from the occlusal portion of each of the at least two tooth crowns.

2. The method according to claim 1, wherein the bracket replica positioned on each of the at least portions of the at least two replica tooth crowns of the model is a replica of an orthondontic bracket configured for positioning on the patient's teeth in an orthontic treatment.

3. The method according to claim 1, wherein the bracket replica positioned on each of the at least portions of the at least two replica tooth crowns of the model is an orthondontic bracket configured for positioning on the patient's teeth in an orthontic treatment.

4. The method according to claim 1, wherein the bracket replica part positioned on each of the at least portions of the at least two replica tooth crowns of the model includes the coronal wing only.

5. The method according to claim 1, wherein the bracket replica part positioned on each of the at least portions of the at least two replica tooth crowns of the model includes the coronal wing and at least a portion of the wire guide, the at least portion of the wire guide reaching up to a middle of a wire-lead through.

6. The method according to claim 1, wherein the model further includes a connection part between each of the at least portions of the at least two tooth crowns and the bracket replica or bracket replica part.

7. The method according to claim 1, wherein producing the at least two trays includes creating initially one impression and dividing subsequently the one impression to obtain the at least two trays.

8. The method according to claim 1, wherein producing the at least two trays includes creating initially at least two impressions, each of the two impressions corresponding to one of the at least two tooth crowns with the arranged bracket replica or bracket replica part thereon.

9. The method according to claim 1, wherein the bracket replica or bracket replica part of each of the at least two tooth crowns being arranged in the model along parallel running straight lines.

10. The method according to claim 1, wherein the at least one impression being created by casting the model with the at least one bracket replica or bracket replica part arranged thereon and using as casting compound.

11. The method according to claim 1, wherein the at least one impression being created by thermoforming a thermoforming film on the model with the at least one bracket replica or bracket replica part arranged thereon.

* * * * *